(12) United States Patent
Won et al.

(10) Patent No.: US 9,064,386 B2
(45) Date of Patent: Jun. 23, 2015

(54) ALARM ENHANCING PROTECTIVE COVER FOR SAFETY INSTRUMENTS WITH OPTIONAL CALIBRATION CHAMBER

(71) Applicant: Industrial Scientific Corporation, Oakdale, PA (US)

(72) Inventors: Tae-yeon Won, Bridgeville, PA (US); Charles Hughes, Moon Township, PA (US); Brad Day, Canonsburg, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 132 days.

(21) Appl. No.: 13/933,426

(22) Filed: Jul. 2, 2013

(65) Prior Publication Data

US 2014/0091939 A1    Apr. 3, 2014

Related U.S. Application Data

(60) Provisional application No. 61/708,839, filed on Oct. 2, 2012.

(51) Int. Cl.

| | |
|---|---|
| *G08B 21/00* | (2006.01) |
| *G08B 3/00* | (2006.01) |
| *G10K 9/22* | (2006.01) |
| *G10K 11/20* | (2006.01) |
| *H04M 1/03* | (2006.01) |

(52) U.S. Cl.
CPC .. *G08B 3/00* (2013.01); *G10K 9/22* (2013.01); *G10K 11/20* (2013.01); *H04M 1/035* (2013.01)

(58) Field of Classification Search
USPC .......... 340/696.6, 540, 632; 361/600, 679.01; 73/1.06, 23.21; 181/187, 191
See application file for complete search history.

(56) References Cited

U.S. PATENT DOCUMENTS

| | | | |
|---|---|---|---|
| 3,960,495 | A | 6/1976 | Tantram |
| 4,406,770 | A | 9/1983 | Chan et al. |
| 4,525,872 | A | 6/1985 | Zochowski |
| 4,587,003 | A | 5/1986 | Tantram et al. |
| 4,775,083 | A | 10/1988 | Burger et al. |
| 4,963,855 | A | 10/1990 | Kojima |
| 5,005,419 | A | 4/1991 | O'Donnell et al. |
| 5,138,559 | A | 8/1992 | Kuehl et al. |
| 5,243,152 | A | 9/1993 | Magid |
| 5,394,094 | A | 2/1995 | Wagner |

(Continued)

FOREIGN PATENT DOCUMENTS

| | | |
|---|---|---|
| GB | 2423400 A | 8/2006 |
| JP | 2002-344602 A | 11/2002 |

(Continued)

OTHER PUBLICATIONS

Anonymous, "Solaris Multigas Detector" Jan. 1, 2005, *Solaris Multigas Manual*, pp. 1- 54.

(Continued)

*Primary Examiner* — Jeffery Hofsass
(74) *Attorney, Agent, or Firm* — Pepper Hamilton LLP (57) ABSTRACT

Methods and systems to redirect the audible and visible signals from alarms on a portable safety device. A cover (10) cooperates with a portable safety device (50) to define a sound chamber (12) that amplifies audible warning signals. A visual alarm guide (14) also is provided. A calibration adapter (500) affords quick and simple bump testing and calibration of the portable safety device.

32 Claims, 9 Drawing Sheets

(56) References Cited

U.S. PATENT DOCUMENTS

| | | |
|---|---|---|
| 5,464,983 A | 11/1995 | Wang |
| 5,662,143 A | 9/1997 | Caughran |
| 5,668,302 A | 9/1997 | Finbow et al. |
| 5,902,467 A | 5/1999 | Wang et al. |
| 5,914,019 A | 6/1999 | Dodgson et al. |
| 6,031,454 A | 2/2000 | Lovejoy et al. |
| 6,055,840 A | 5/2000 | Warburton |
| 6,096,186 A | 8/2000 | Warburton |
| 6,119,186 A | 9/2000 | Watts et al. |
| 6,165,347 A | 12/2000 | Warburton |
| 6,284,545 B1 | 9/2001 | Warburton et al. |
| 6,319,375 B1 | 11/2001 | Warburton |
| 6,338,266 B1 | 1/2002 | Warburton |
| 6,370,940 B2 | 4/2002 | Warburton |
| 6,402,933 B1 | 6/2002 | Dowling |
| 6,428,684 B1 | 8/2002 | Warburton |
| 6,435,003 B1 | 8/2002 | Warburton |
| 6,442,639 B1 | 8/2002 | McElhattan et al. |
| 6,447,659 B1 | 9/2002 | Peng |
| 6,629,444 B2 | 10/2003 | Peng |
| 6,632,674 B1 | 10/2003 | Warburton |
| 6,666,963 B1 | 12/2003 | Peng et al. |
| 6,679,094 B2 | 1/2004 | Wang et al. |
| 6,742,382 B2 | 6/2004 | Warburton et al. |
| 6,888,467 B2 | 5/2005 | Green et al. |
| 6,997,347 B2 | 2/2006 | Peng et al. |
| 7,007,542 B2 | 3/2006 | Wang et al. |
| 7,041,256 B2 | 5/2006 | Wang et al. |
| 7,275,411 B2 | 10/2007 | Peng |
| 7,281,404 B2 | 10/2007 | Peng et al. |
| 7,534,333 B2 | 5/2009 | Khalafpour et al. |
| 7,736,479 B2 | 6/2010 | Prohaska et al. |
| 7,778,431 B2 | 8/2010 | Feng et al. |
| 7,880,607 B2 | 2/2011 | Olson et al. |
| 8,086,285 B2 | 12/2011 | McNamara et al. |
| 8,174,557 B2 | 5/2012 | Kieffer et al. |
| 8,180,075 B2 | 5/2012 | Nelson et al. |
| 2001/0050612 A1 | 12/2001 | Shaffer |
| 2002/0008625 A1 | 1/2002 | Adams et al. |
| 2002/0009195 A1 | 1/2002 | Schon |
| 2002/0126002 A1 | 9/2002 | Patchell |
| 2003/0107483 A1 | 6/2003 | Kano |
| 2004/0119591 A1 | 6/2004 | Peeters |
| 2004/0128823 A1 | 7/2004 | Mole |
| 2004/0145485 A1 | 7/2004 | Tice |
| 2004/0215396 A1 | 10/2004 | Christie et al. |
| 2005/0202582 A1 | 9/2005 | Eversmann et al. |
| 2005/0252980 A1 | 11/2005 | Kim |
| 2006/0224357 A1 | 10/2006 | Taware et al. |
| 2007/0078608 A1 | 4/2007 | Broy |
| 2007/0171042 A1 | 7/2007 | Metes et al. |
| 2008/0061965 A1 | 3/2008 | Kuhns et al. |
| 2008/0094210 A1 | 4/2008 | Paradiso et al. |
| 2008/0240463 A1 | 10/2008 | Florencio et al. |
| 2009/0115654 A1 | 5/2009 | Lo et al. |
| 2009/0312976 A1 | 12/2009 | Bingham et al. |
| 2010/0072334 A1 | 3/2010 | Le Gette et al. |
| 2010/0170795 A1 | 7/2010 | Cowburn et al. |
| 2011/0316699 A1 | 12/2011 | Arunachalam |
| 2012/0018303 A1 | 1/2012 | Bordo et al. |

FOREIGN PATENT DOCUMENTS

| | | |
|---|---|---|
| WO | WO 95/26492 A1 | 10/1995 |
| WO | WO 01/82063 A1 | 11/2001 |
| WO | WO 2011/163604 A1 | 12/2011 |
| WO | WO 2014/055147 A2 | 4/2014 |

OTHER PUBLICATIONS

Anonymous, "Solaris Multigas Detector" Oct. 1, 2006, *Solaris Multigas Manual*, pp. 1-4.

Ding et al., "Redundant Sensor Calibration Monitoring using Independent Component Analysis and Principal Component Analysis",*Real Time Systems*, Jan. 1, 2004, 27:27-47.

Enmet, "RECON/4 Manual" Enmet Corporation (Ann Arbor, MI), Jun. 22, 2009, Manual Pat No. 80006-004, pp. 1-10.

ALARM ENHANCING PROTECTIVE COVER FOR SAFETY INSTRUMENTS WITH OPTIONAL CALIBRATION CHAMBER

CROSS-REFERENCE TO RELATED APPLICATIONS

The present application claims the benefit under 35 USC 119(e) of prior U.S. Provisional Application 61/708,839 titled "Alarm Enhancing Protective Cover For Safety Instruments With Optional Calibration Chamber" filed Oct. 2, 2012 by Won et al., which is incorporated herein by reference in its entirety.

BACKGROUND OF THE INVENTION

1. Technical Field of the Invention

The presently disclosed invention pertains generally to a protective cover for a portable safety instrument, and more specifically to a protective cover that enhances the audible and visible output from alarms on such a device.

2. Background of the Invention

Portable safety devices are often used and worn by individuals who work in extreme environments. Such safety devices may monitor for concentrations of gases that are toxic, combustible, or contain volatile organic compounds (VOCs), or for oxygen deficits. Once a threshold limit is reached, the portable devices may actuate a visible, audible or vibrational alarm to warn the individual of potential danger.

As an example, workers at oil fields, oil production sites and refineries are often exposed to hydrogen sulfide, $H_2S$, a colorless gas that at low concentrations has the well-known odor similar to rotten eggs. At higher concentrations, $H_2S$ rapidly deadens the sense of smell (150 ppm), can cause immediate collapse and unconsciousness (750 ppm), and even lead to cardiac arrest and death (1000 ppm). Because of the poor sensory warning (e.g. lack of smell when at toxic levels), extreme toxicity, and pervasiveness of this hazard, workers are often required to wear a personal gas detector for $H_2S$ at all times while they are at a work site where there is exposure potential.

The usefulness of a portable safety device, however, depends on the user's recognition of and response to the warning signals from the detectors as well as the accuracy of such detectors. For example, the worker must be able to hear the audible signal even under the extreme and often very loud conditions of many work environments, such as the oil refineries mentioned above. Furthermore, in many environments, it may be difficult for the worker to observe a visible signal due to goggles or ventilation equipment, or simply because the type of work they perform impedes such an ability. Vibrational alarms may not be detected by a worker wearing extra protective clothing.

Failure of portable safety devices to provide an accurate audible, visible or vibrational alarm is often linked to infrequent bump testing and calibration. It is vital to worker safety that such instruments are maintained and calibrated properly. In use, however, the worker may not take the time to perform such testing if it requires undue additional time and/or difficult procedures.

One approach to provide enhanced signal output from a portable safety device would be to add external speakers or additional lights to amplify the audible and/or visible alarms. The difficulty with such a solution is the increased size and weight of the portable device that such added features bring, and the increased power requirement placed on the instrument's battery to support such additional features.

Unpowered sound conducting structures have been proposed in the prior art to enhance the sound directed to a portable device such as a phone. For example, U.S. Pat. Nos. 1,797,891 and 5,778,062 both teach a bowl shaped reflector that may be positioned over the microphone of a phone to enhance the sound quality of the user's voice as they speak into the phone. The reflector acts to dampen environmental sounds while amplifying the user's voice.

Similar ideas have been disclosed to enhance the sound emanating from a mobile phone's internal speakers. U.S. Pat. No. 8,086,285 describes a mobile phone having a sound reflector that may be extended outward from the case near the phone's speaker to enhance the quality of the sound produced. The sound reflector is shown, however, to increase the length of the mobile phone by an additional 50%. U.S. Pat. No. 8,180,075 teaches a mobile phone housing that forms part of a resonance pipe that enhances sound produced by the phone's internal speakers in the range of 400-500 hertz (Hz).

Sound reflectors have also been disclosed as safety devices. For example, U.S. Pat. No. 5,243,152 describes a baffle for a personal alarm that may redirect the sound from the alarm so that it can't be muffled, such as in the case that an attacker places a hand over the speaker on the device. U.S. Pat. No. 4,963,855 teaches a set of passageways that redirect and increase the sound from a fire alarm in the manner of a resonance tube.

Non-portable unpowered sound conducting structures have also been proposed in the prior art. For example, U.S. Pat. App. No. 2002/0009195 describes a mounting stand for a mobile phone that includes a sound conducting horn assembly to amplify sound from the phones internal speakers. U.S. Pat. No. 7,778,431 teaches a mounting stand for a mobile phone that enhances the sound generated by the phone's internal speakers through the use of a resonator shell that includes a cavity and a reflecting surface. The cavity has a volume of 100 to 200 cm$^3$ and provides a resonant frequency response which is tunable to between 1500 and 500 Hz; the greater the size of the internal cavity the lower the frequency.

While each of the aforementioned patents and application provide methods to enhance the sound quality of a portable device, they all require additional apparatus that is comparable in size to the portable device itself. For example, the resonance shell disclosed in U.S. Pat. No. 7,778,431 comprises a cavity of 100 to 200 cm$^3$. If such a cavity were added to a standard portable device, it would require the addition of between 1 to 3 inches of thickness to the device. Further, the sound reflector of U.S. Pat. No. 8,086,285 would add considerable length to a portable device and may not direct the sound toward an individual who is wearing the device, as is frequently the case for portable safety devices.

Smaller equipment is known, such as the resonance pipe of U.S. Pat. No. 8,180,075, that amplifies sound in the range of 400-500 Hz. However, that apparatus is directed to sound in the frequency range of the spoken voice (e.g. typically in the range of 80 to 1200 Hz). None of the prior art describes apparatus that is capable of amplifying sound at resonance frequencies that are commonly used for alarms (2000-4500 Hz). Further, the prior art does not describe sound amplification that is suitable for addition to a portable device that must be kept small and lightweight, nor does it describe methods for amplifying the signal from a visible alarm.

The prior art has disclosed sound redirecting elements such as the sound reflectors taught in U.S. Pat. Nos. 5,243,152 and 8,086,285, the sound tubes taught in U.S. Pat. Nos. 4,963,855 and 8,180,075 and U.S. Pat. App. 2002/0009195, and the sound chamber taught in U.S. Pat. No. 7,778,431. However, none of those patents describe redirecting sound pressure waves from an audible alarm in the resonance frequency range of 2000 to 4500 Hz. Nor do they describe redirecting sound pressure waves so as to enhance the wearer's detection of the audible signal in an environment of a high level of background noise.

There was also a need in the prior art to make functionality testing and calibration of improved portable gas monitors simple and fast. A correlation between bump test intervals and gas detector failures has been established ("Why bump testing saves lives," D. Wagner, Industrial Scientific Corporation). An extension of the bump test interval from 1 day to 1 month was found to correlate to a 4 to 5 fold increase in the probability of device failure. This increase in failure rate obviates the advantages of a calibration gas chamber that is simple to attach and easy to use.

Accordingly, there was a need in the art for an unpowered apparatus to amplify the audible and visible alarms of a portable safety gas monitoring device. Further, there was a need in the art for a portable testing apparatus that makes bump testing and calibration of a portable safety device faster and more straightforward.

SUMMARY OF THE INVENTION

The presently disclosed invention provides a protective cover for a portable safety device. The protective cover includes a sound chamber that enhances the audible alarm of the device and, optionally, a visual alarm guide that enhances visibility of an optical alarm. The protective cover is formed of thin impact-resistant materials that protect the portable safety device from mechanical impact and from extreme temperature. The protective cover adds limited additional size to the device. The sound chamber amplifies audible alarms on the portable safety device in a range of resonance frequencies that is especially useful for safety alarms, about 3500±250 Hz. Further, the visual alarm guide redirects light from a visible alarm to the user's field of view so that a user may more easily detect the signal.

The presently disclosed invention includes a sound chamber that is small relative to the prior art. The sound chamber has an exit opening which represents 40% of the volume (1.2 $cm^2$ opening on a 3 $cm^3$ sound chamber). The sound chamber functions optimally in the resonance frequency range commonly used for audible safety alarms (2800 to 4500 Hz). While human hearing normally perceives sounds from 20 Hz to 20,000 Hz, hearing is most sensitive to sounds in the 3000 Hz to 4000 Hz range. Sounds outside of that frequency range must be of greater amplitude to be distinguished as relatively loud. The sound chamber of the presently disclosed invention functions in the optimal frequency range for the human ear.

Embodiments of the alarm enhancing protective cover may further include a calibration gas chamber that affords easy calibration or bump testing of a gas sensor in a portable safety device such as a gas monitor.

Thus, according to its major aspects, and briefly stated, the presently disclosed invention includes an alarm enhancing protective cover for a portable safety device that includes an audible alarm. The portable safety device has a casing with a speaker port that is located on a front face of the casing. The alarm enhancing cover may comprise a front panel that has an exit opening, a sound redirecting surface that is located adjacent to said exit opening, and additional panels that are connected to the perimeter of the front panel. The additional panels may be adapted to removeably engage respective sides of the portable safety device. When attached to the portable safety device, the cover cooperates with the portable safety device to define a sound chamber having a sound chamber exit opening.

The front panel of the protective cover may be located oppositely from the front face of the casing of the portable safety device such that the sound chamber provides an amplified resonance frequency response between 2000 and 4500 Hertz, preferably between 3250 and 3750 Hz. Further, the sound redirecting surface may be located oppositely from the speaker port of the front face of the casing and oriented at an angle with respect to the front face of the casing. In this way, the front panel redirects sound from the speaker in the portable safety device in a direction that is parallel to or lateral with respect to the front face of the casing for the portable safety device. Preferably, the angle may be between 40° to 50°.

The sound chamber may have a volume of about 2.7 $cm^3$ to 3.3 $cm^3$ and an exit opening that defines an opening area of 1.05 $cm^2$ to 1.35 $cm^2$. Further, the sound chamber may amplify sound output from the audible alarm on the portable safety device by about 8 to 12 dB, or by about 10 to 12%.

The alarm enhancing protective cover may further comprise at least one surface for reflecting visible light. The light reflecting surface is located on the front panel adjacent to the exit opening. The reflecting surface may be located oppositely from a visible alarm on the front face of the portable safety device. The at least one reflecting surface may be sloped at an angle with respect to the front face of the casing of the portable safety device such that the front panel redirects light from the visible alarm of the portable safety device in a direction that is parallel to or lateral with respect to the front face of the portable safety device. This angle may be between 40° to 50°. The light reflecting surface may be a mirrored surface.

The alarm enhancing protective cover may be formed of high-impact molded material, and may have openings that afford access to at least one of a button, a viewing screen, a sensor, a light and an access point located on the portable safety device. The sensor may be a gas sensor, and the access points may be any of a battery charging port, an antenna, a microphone, a SIM card slot, a memory card slot, and a docking port terminal.

For instances when the portable safety device is a portable gas monitor, the alarm enhancing protective cover may further comprise a calibration adapter that has side walls and a gas inlet port. The side walls of the calibration adapter may be adapted to removeably engage a front portion of the cover, the calibration adapter being located to cover the exit opening on the front panel of the cover. The calibration adapter cooperates with the cover and the casing at times when the side panels of the cover engage the respective sides of the portable safety device to define a calibration chamber.

The presently disclosed invention also includes methods to amplify an alarm on a portable safety device, improve effectiveness of a portable safety device, and calibrate a portable safety device.

Other objects and advantages of the presently disclosed invention will become apparent to those of skill in the art as the description of a presently disclosed embodiment of the invention proceeds.

BRIEF DESCRIPTION OF THE DRAWINGS

Aspects, features, benefits and advantages of a preferred embodiment of the presently disclosed invention will be apparent with regard to the following description, examples, appended claims, and accompanying drawings. In the following figures, like numerals represent like features in the various views. It is to be noted that features and components in these drawings, illustrating the views of embodiments of the presently disclosed invention, unless stated to be otherwise, are not necessarily drawn to scale.

DESCRIPTION OF PRESENTLY PREFERRED EMBODIMENTS

Figure 1:
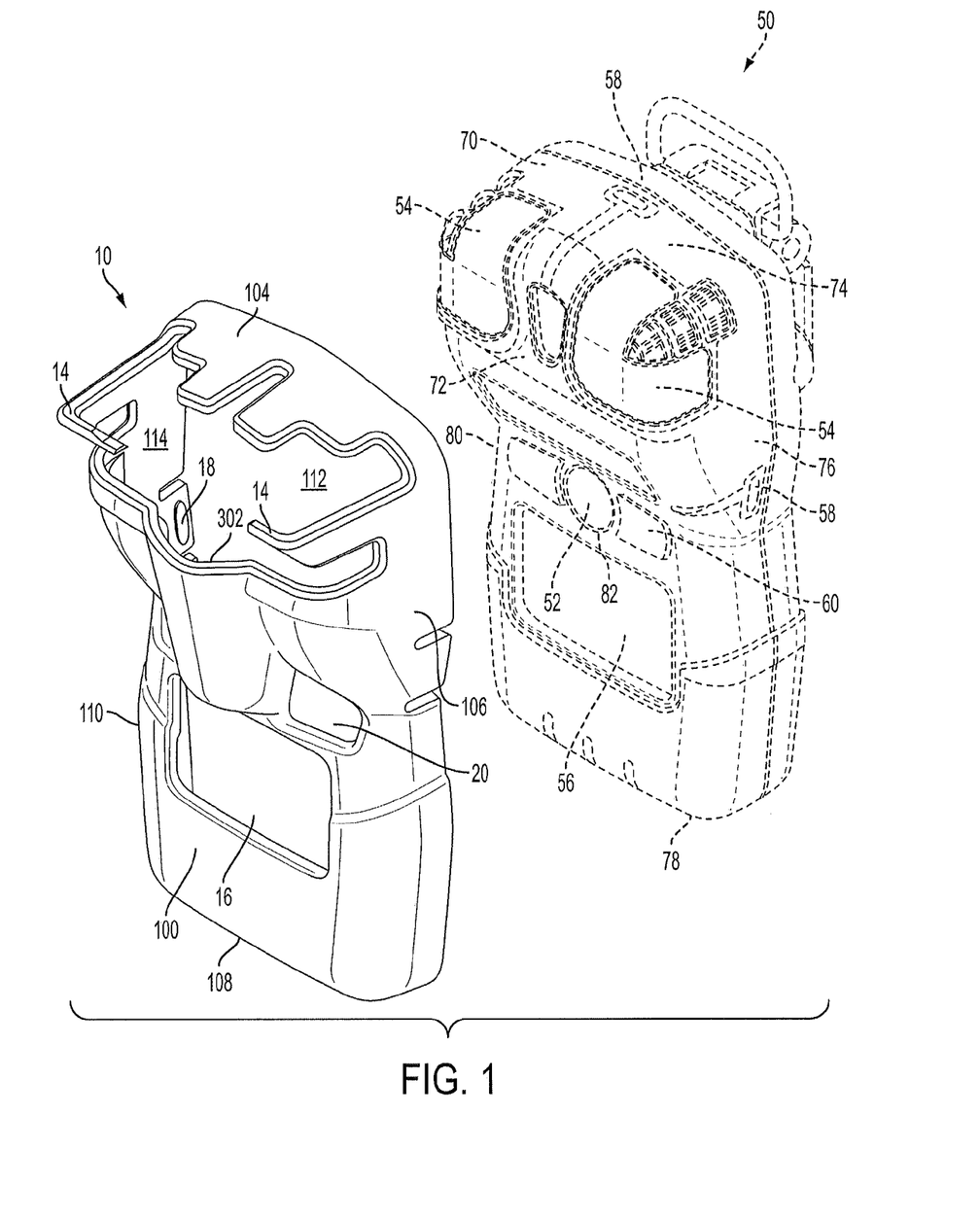
FIG. 1 illustrates a perspective view of an exterior facing side of an alarm enhancing protective cover in accordance with certain aspects of the presently disclosed invention including a portable safety device.

Referring now to the drawings, embodiments of the alarm enhancing protective cover of the presently disclosed invention are shown in FIGS. 1-5 generally designated by reference numeral 10. FIG. 1 shows a perspective view of cover 10 in line with a portable safety device 50 before being attached. Portable safety device 50 may be a single gas monitor, a multi-gas monitor, or any other portable instrument or device which may comprise an audible and/or visible alarm, hereinafter collectively referred to as a "device". Device 50 may be carried by a user, worn by a user, such as on a lanyard, or attached to an article of the user's clothing.

Device 50 includes a case 70 that defines a front face 72 and side faces 74, 76, 78 and 80. Side faces 74, 76, 78 and 80 are each connected to front face 72. Front face 72 includes a port 82 that is located over a speaker 52 that is a component of the audible alarm of device 50.

Alarm enhancing protective cover 10 includes a front panel 100 that includes a sound redirecting surface 302. Cover 10 further includes side panels 104, 106, 108, and 110 that are respectively each connected to front panel 100 at the perimeter of the font panel. Side panels 104, 106, 108 and 110 cooperate with front panel 100 to define a cavity 112. The front face 72 and at least a portion of side faces 74, 76, 78 and 80 of case 70 are receivable in cavity 112.

Side panels 104, 106, 108 and 110 include structure 18 for removably engaging side faces 74, 76, 78 and 80 respectively. At times when side panels 104, 106, 108 and 110 engage respective sides of the case of the portable safety device 50, the front panel 100 of cover 10, including sounding reflecting surface 302, is disposed apart from the front face of the cover of the portable device 50 to define a sound chamber 12 between the front panel 100 of cover 10 and the front face 72 of case 70. At least one of the side panels 104, 106, 108 and 110 is at least partially defining an exit opening 114 for the sound chamber 12. Sound is output from sound chamber 12 through exit opening 114 in response to sound waves being input to sound chamber 12 at port 82 of the front face 72 of case 70.

In the example of the preferred embodiment, side panel 104 particularly defines exit opening 114 in cooperation with front panel 100 such that side panel 104 and front panel 100 cooperate to define exit opening 114.

Preferably, device 50 includes an optical alarm 120 that generates a signal of visible light in response to sensing a hazardous condition. The front panel 100 of cover 10 includes an optical alarm grade 14 that includes additional surface 122 and 124 that are positioned so as to be illuminated by the visible light from optical alarm 120. Surface 122 and 124 are mirrored surfaces that are sloped at an angle with respect to the incidence of light from the optical alarm 12 such that surfaces 122 and 124 redirect light from the optical alarm into the normal field of view of the user. In cases when the user carries device 50 on their person in a generally vertical position, the light reflecting surfaces 122 and 124 define an angle of 40° to 50° with respect to the surface of the front face 72 of case 70.

Cover 10 is adapted for a conforming fit with the outer portion of device 50. Cover 10 may protectively enclose a side of device 50 which may have at least one audible alarm 52, generally the front side of the device. Device 50 may also have at least one visible alarm 54. Such alarms may be activated when the device senses a threshold limit has been reached and/or surpassed. In the case of a single gas monitor, for example, the alarms may be activated when a threshold limit of the single gas which the device is designed to detect has been reached and/or surpassed. The device may also comprise a viewing screen 56, various other control buttons 60, and attachment features 58 which may provide location and means for attachment of cover 10.

Cover 10 may be molded of any hard plastic, hard rubber, or the like that may provide for high impact strength and offer added protection to device 50 in the event that it is dropped or otherwise bumped. Further, the molded cover material may provide a natural decorative effect (e.g. three-dimensional raised regions, embossed regions, varied colors). Other decorative effects may be applied by, for example, painting, or the application of additional pre-colored moldable material layers.

Cover 10 may partially define sound chamber 12 which may amplify the sound of audible alarm 52 on device 50. When cover 10 is attached to device 50, sound chamber 12 may have an internal cavity and exit opening 114. Exit opening 114 may be positioned on cover 10 so that sound pressure waves are emitted from sound chamber 12 in the direction of the user. Sound chamber 12 may work in concert with any audible alarm 52 known in the art such as, for example, a speaker, buzzer, siren, bell, air horn, etc. Furthermore, audible alarm 52 may produce sound in any frequency range perceived by human hearing, typically between 20 Hz and 20,000 Hz.

Cover 10 may further comprise at least one visual or optical alarm guide 14 that may redirect the signals from visible alarms 54 of device 50. The signals from the visible alarms 54 may fall within any part of the electromagnetic spectrum that is detectable by human vision, typically between wavelengths from about 390 to 700 nm, referred to as visible light.

The signals from visible alarms 54 may be redirected in a fixed manner or may be user controlled. For example, visual alarm guide 14 of FIG. 1 would redirect light from visible alarm 54 in the direction of the user's normal horizontal field of vision when device 50 is worn vertically (as shown) anywhere below the users normal horizontal field of vision (e.g. on the user's belt, shirt or coat). If the user preferred to wear device 50 above their field of vision (e.g. on a hat), visual alarm guide 14 may be rotated (turned 180°) so that signal (light) from visible alarms 54 would be redirected to the user's normal horizontal field of vision.

In certain embodiments, the signal from visible alarm 54 may be directed to a user's field of vision using a light tube, light pipe, prism light guide, or optical fibers (not shown), Such would allow the light from visible alarm 54 to be collected and redirected to a distal end of the light tube, light pipe, light guide or optical fibers which may be placed within the user's normal horizontal field of vision, such as attached to a helmet or hat, or on a pair of goggles or glasses.

Cover 10 may have a viewing screen access opening 16 to provide unobstructed inspection of and access to viewing screen 56 on device 50. Viewing screen access opening 16 may be sized to border viewing screen 56, may be larger than the viewing screen or may be smaller than the viewing screen. Further, viewing screen access opening 16 may also provide access to buttons or a keypad on a front surface of device 50.

Additional openings 20 may be provided in cover 10 to provide access to various buttons 60 or ports on device 50. For example, additional openings may be provided for sensors, such as a gas sensor region, battery charging ports, various antennae, memory card slots, user accessible buttons, and docking port terminals on the device. Openings for these in the cover may align and register with the corresponding ports or regions of the device. While openings (16, 20) are shown in a specific arrangement on cover 10, any arrangement and number of openings necessary to accommodate a specific device are envisioned.

Cover 10 is adapted to fit over a surface on the device 50 that includes audible alarm 52. For most devices 50 this may be the front surface. Further, while cover 10 is shown in the figures to be generally rectangular in shape, any shape is envisioned that may cover device 50 and provide a sound chamber 12 and, optionally, a visual alarm guide 14. As is shown in FIG. 1, cover 10 fits over the front face 72 and four side faces 74, 76, 78 and 80 connected to front face 72 of device 50. At least one mating attachment element 18 on cover 10 may be used to securely but releasably engage at least one attachment feature 58 on device 50. Attachment element 18 may be a detent device or a threaded fastener. Additionally, attachment elements 18 may be formed on any of the panels of cover 10, such as on an internal side of cover 10 as shown in FIG. 1. Mated attachment elements 18 and features 58 may engage each other mechanically using any fastening means known in the art including, but not limited to, buckles, clasps, hooks, mated indentations and protrusions, mated protrusions, magnetic snaps, or hook and loop closures. In a preferred embodiment, attachment of cover 10 to device 50 may be done manually without the use of tools.

Figure 2A:
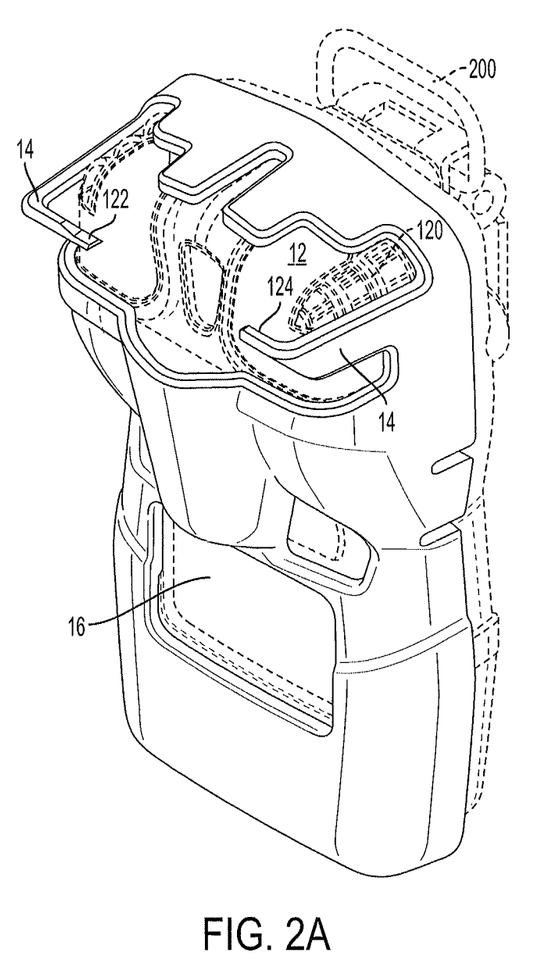
FIG. 2A illustrates a perspective view of an exterior facing side of an alarm enhancing protective cover in accordance with certain aspects of the presently disclosed invention including a portable safety device.
Figure 2B:
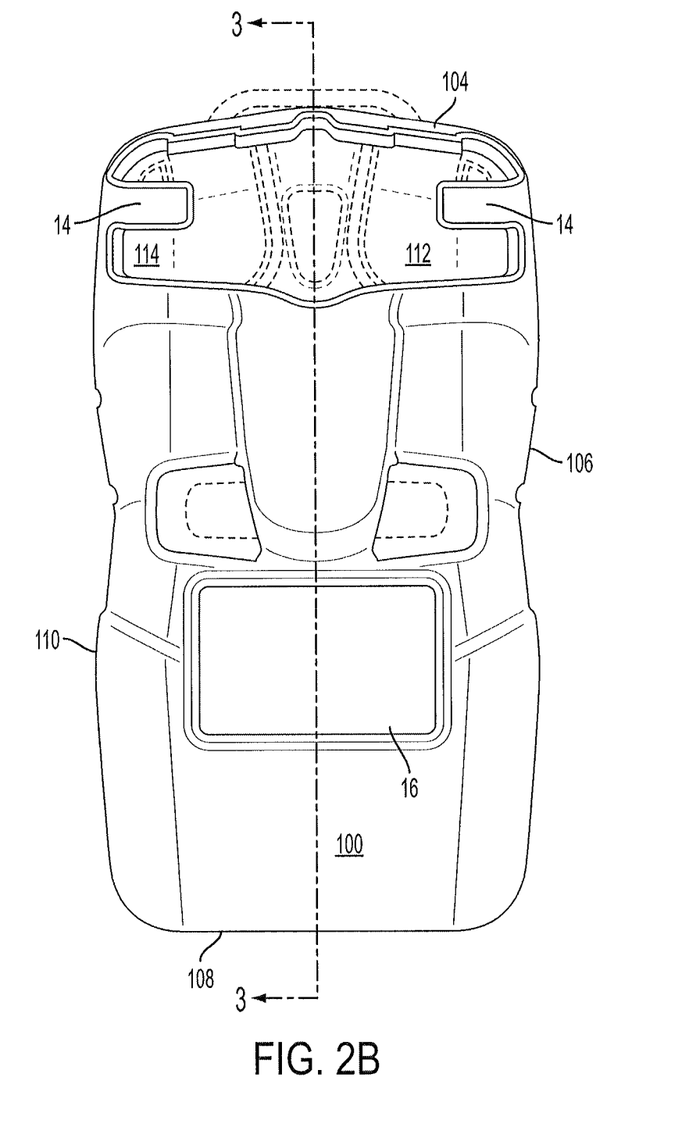
FIG. 2B illustrates a front view of an exterior facing side of an alarm enhancing protective cover in accordance with certain aspects of the presently disclosed invention including a portable safety device.
Figure 2C:
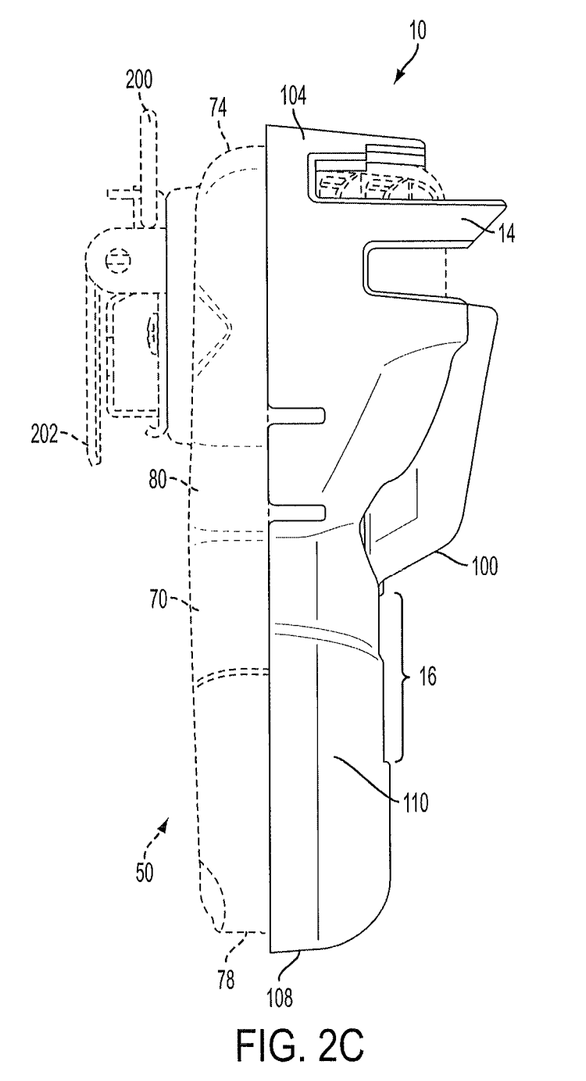
FIG. 2C illustrates a side view of an exterior facing side of an alarm enhancing protective cover in accordance with certain aspects of the presently disclosed invention including a portable safety device.

FIGS. 2A-C are perspective views of an embodiment of cover 10 of the presently disclosed invention attached to device 50. Visual alarm guides 14 of cover 10 are shown positioned adjacent to visible alarms 54 on device 50. Also shown are sound chamber 12 and viewing screen access opening 16 of cover 10, as well as means for attachment of device 50 to a user, such as a loop 200 and clip 202.

Figure 3:
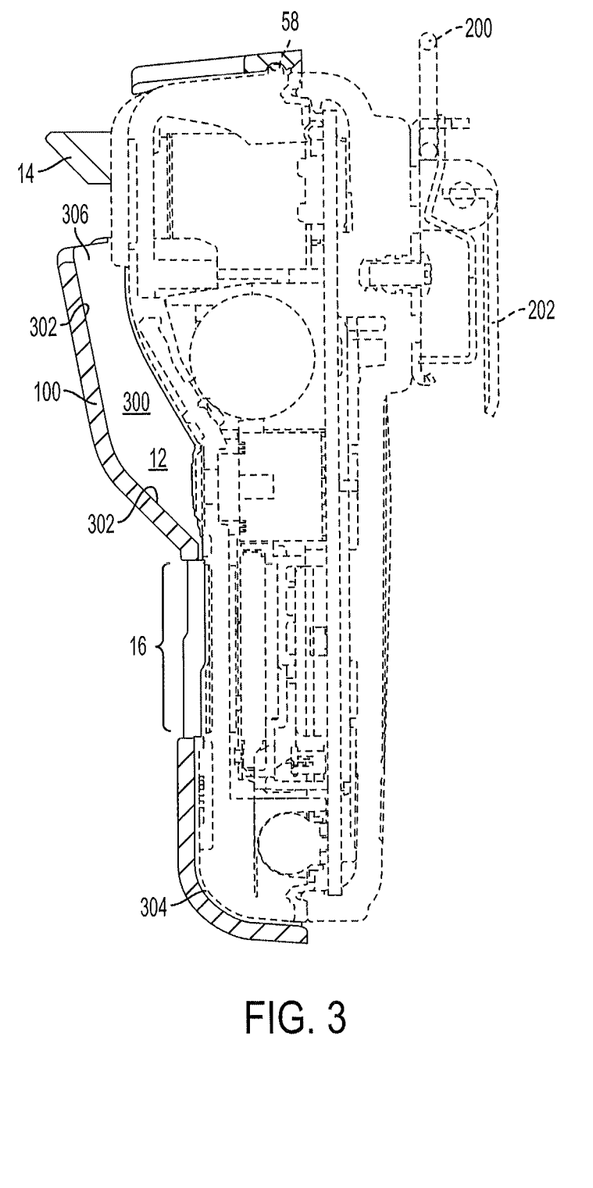
FIG. 3 illustrates a sectional view of the alarm enhancing protective cover shown in FIG. 2B in accordance with certain aspects of the presently disclosed invention including a portable safety device.

FIG. 3 is a sectional view of cover 10 attached to device 50 taken along line 3-3 as shown in FIG. 2B. A single attachment feature 58 is shown as a protrusion on a top surface of device 50 that is orthogonal to the face of device 50. Attachment feature 58 mates with an indent (attachment element) on an inner surface of the cover 10 that is orthogonal to the face surface of cover 10. Also shown are loop 200 and belt clip 202 which may aid in attachment of device 50 to a user's clothing or a lanyard.

Sound chamber 12 may be positioned adjacent to at least a portion of audible alarm 52 such as a speaker on device 50, and may have a sound redirecting or sound reflecting surface 302 that is a sloped surface that is located opposite from the speaker 52 of audible alarm 52 and port 82 of front face 72. In certain embodiments of cover 10, sloped surface 302 may be aligned above audible alarm 52 at an angle of about 45°±5° relative to the orthogonal direction from audible alarm 52. The angle of sloped surface 302 may be changed to accommodate varied exit directions for the sound pressure waves emitted from audible alarm 52 and amplified in sound chamber 12.

Further, sound chamber 12 may define an internal chamber 300 and an exit opening 306 that is at least partially formed and by cover 10 at times when it is attached to device 50, as discussed above. While various dimensions and configurations of sound chamber 12 are envisioned, a preferred embodiment of sound chamber 12 of the disclosed invention may fit on a portable safety device such as the Tango™ TX1 offered by Industrial Scientific Corporation. The chamber 300 of cover 10 may be designed to have an internal volume of about 3 $cm^3$±10%, an exit opening 306 having a surface area of about 1.2 $cm^2$±10%, and a distance from audible alarm 52 to exit opening 306 of about 3 cm±10%. In such an embodiment, sound pressure may be amplified in sound chamber 12 by about 10 to 12%, corresponding to about 8 to 12 decibels (dB), at the resonance frequency range of 2000 to 4500 Hz.

Sound chambers known in the prior art are larger than the chamber 300 herein disclosed. For example, the sound chamber taught in U.S. Pat. No. 7,778,431 has an internal cavity volume of 100 to 200 $cm^3$ with an exit opening of between 5 and 30 $cm^2$, and provides a resonant frequency response which is tunable to between 500 and 1500 Hz. Sound chamber 300 enhances resonance frequency response in the range of 2000 to 4500 Hz.

The angle of redirecting surface 302 (FIG. 3) of the presently disclosed invention is optimal for enhancing resonance frequency response in the frequency range commonly used for audible alarms (see FIGS. 6 and 7) and for redirecting the signal so that it may be optimally detected by a person using cover 10.

Figure 4:
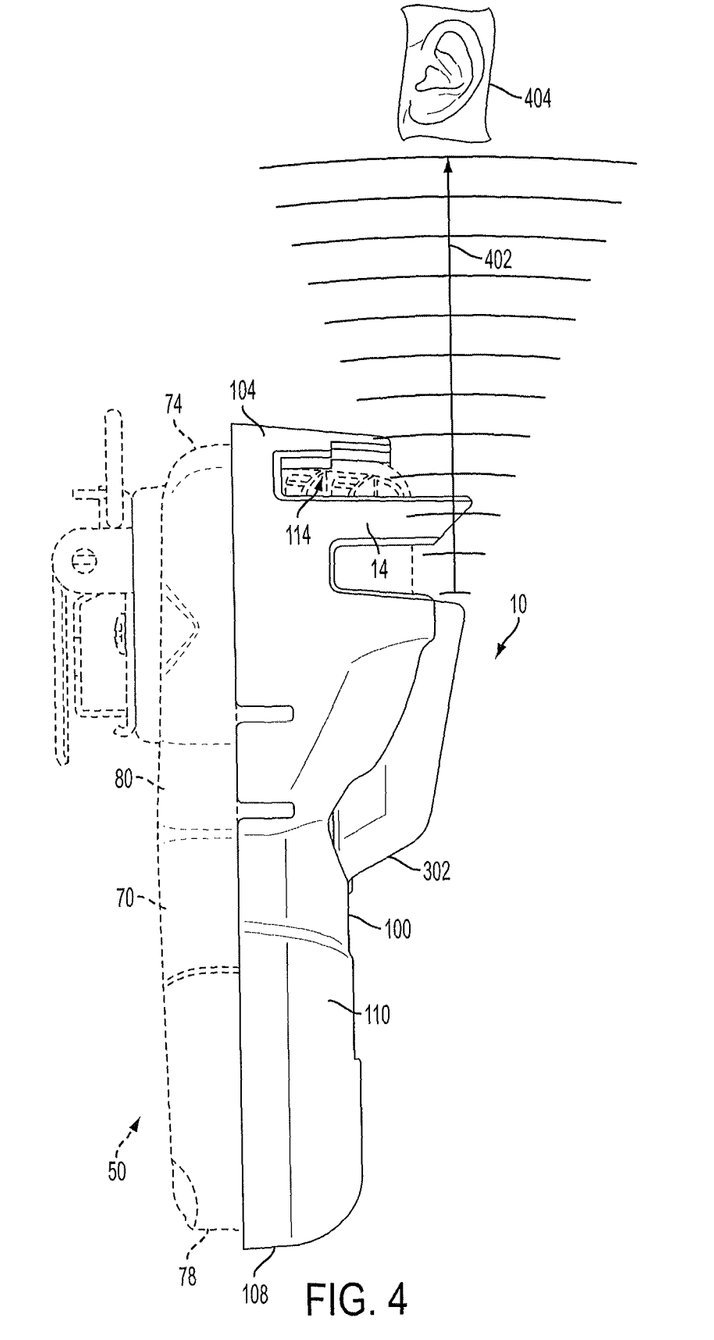
FIG. 4 illustrates a side view of an exterior facing side of an alarm enhancing protective cover in accordance with certain aspects of the presently disclosed invention including a portable safety device and showing sound waves directed to a user's ear.

With reference to FIG. 4, sound chamber 12 is shown to redirect sound from an audible alarm in the direction 402 toward the user's field of hearing, represented by ear 404. The sound pressure waves from the alarm may be redirected by redirecting surface 302 and focused to exit sound chamber 12 in a direction 402 most optimal for the user to detect the sound (sound waves shown to impinge on user's ear 404). In certain embodiments of cover 10, sound chamber 12 may be designed so that sound pressure waves from the audible alarm are redirected in a different direction, such as may be the case if device 50 were to be worn on a user's hat, arm or shoulder or if the user carries it on their person in a non-conventional orientation. As an example, if device 50 is worn on a user's hat, the exit opening 306 (FIG. 3) of the sound chamber 12, as well as the angle of redirecting surface 302, may be rotated 180° relative to what is shown in FIGS. 1-5.

Referring back to FIG. 3, visual alarm guide 14 may have a reflecting surface that is sloped. The sloped surface may be aligned adjacent to visible alarm 54 on device 50 at an angle of about 45°±5° relative to direction of optical signals propagating from the alarm. Such an angle is selected to optimize signal detection for a user looking down at device 50, such as if the device is worn on a user's belt or around the neck on a lanyard. In the event that device 50 is placed at an alternate location, the angle of the reflecting surface on visual alarm guide 14 may be changed to optimize user detection, as discussed above. Such a change in angle may be accomplished in a static manner, or may be implemented by providing visual alarm guide 14 with means for rotation. Further, to enhance the signal from visible alarm 54 on device 50, the reflecting surface of visual alarm guide 14 may be a mirror or composed of any other highly reflective material known in the art.

FIG. 3 also shows a gap 304 between the inside surface of cover 10 and case 70 of device 50. Gap 304 may aid in further protecting device 50 against damage if dropped or bumped. Additionally, gap 304 may act as a thermal barrier that protects device 50 against damage if exposed to temperature extremes. In a preferred embodiment, gap 304 may be between 0.5 to 1 mm.

Figure 5:
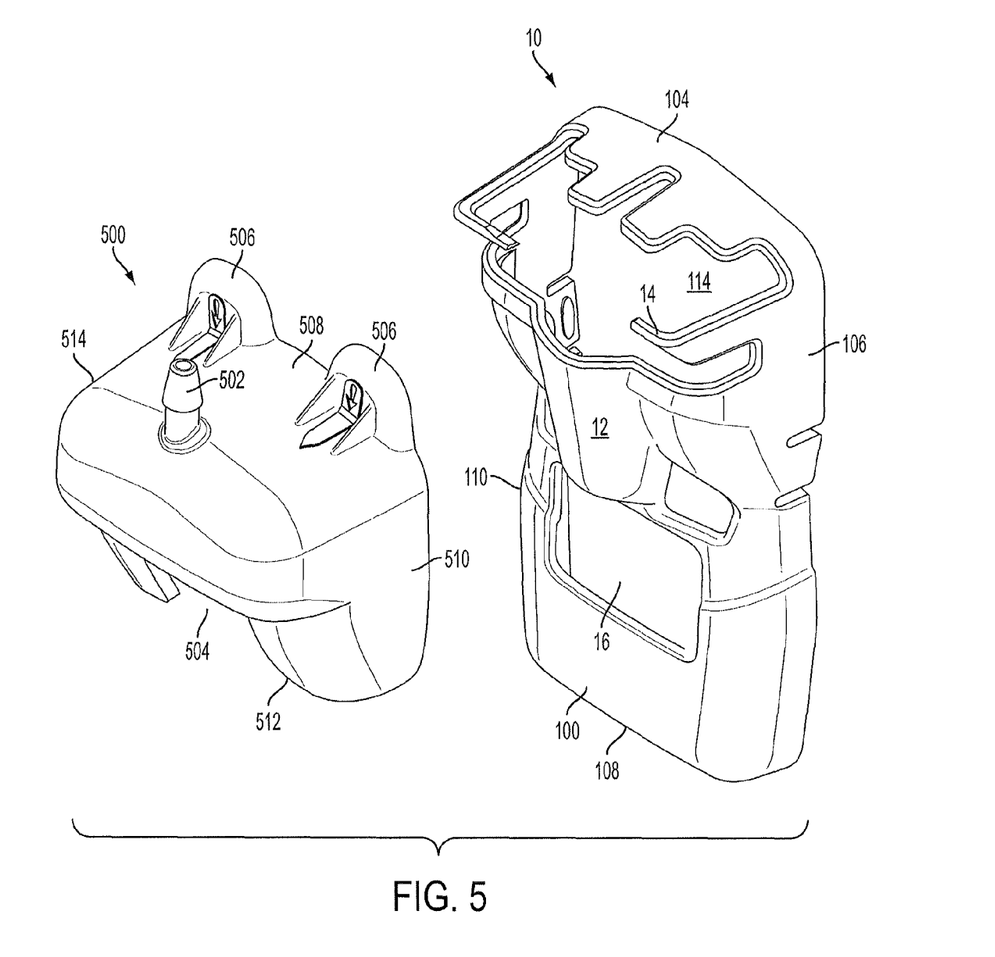
FIG. 5 illustrates a perspective view of an exterior facing side of a calibration adapter attachment including an alarm enhancing protective cover in accordance with certain aspects of the presently disclosed invention.

FIG. 5 depicts a calibration adapter 500 in line with the alarm enhancing protective cover 10 of the presently disclosed invention. A recessed area 504 in calibration adapter 500 receives at last the portion of cover 10 that defines sound chamber 12 so as to cover exit opening 114. Also shown are sound chamber 12, visual alarm guide 14, and viewing screen access opening 16 of cover 10 for reference.

Calibration adapter 500 may be adapted in size to closely fit on a front portion of alarm enhancing cover 10 which is adjacent to a gas sensor region on portable safety device 50 when cover 10 is attached to the device. Preferably, calibration adaptor 500 has side walls 508, 510, 512, and 514 and a gas inlet port 510. Side walls 508, 510, 512 and 514 are adapted to removably engage at least a portion of cover 10 so as to cover exit opening 114. When attached, the calibration adapter 500, cover 10 and front face 72 of case 70 cooperate to define a calibration chamber around the gas sensor. The calibration adapter 500 includes a gas inlet port 502 that may be used to inject a gas into the calibration chamber such that gas sensors on device 50 are exposed to known concentrations of a target gas.

Typically, the gas is supplied from compressed gas cylinders to calibration adaptor 500 for bump testing or for calibrating the device. Other gas sources for calibrating gas monitors, such as permeation ovens and electrochemical gas generators could also be used. In most cases, the gas is delivered to calibration adapter 500 via a tube attached to gas inlet port 502. Therefore, it is advantageous if gas inlet port 502 of calibration adapter 500 contains a receptacle to which one or more common sizes of flexible tubing can be attached. This receptacle is most conveniently a barbed fitting and is designed to be part of the gas inlet port 502. Typical tubing sizes are 0.125, 0.375 and 0.25 inches (approximately 3 mm, 5 mm, 6 mm) outside diameter tubing, but other sizes are also envisioned. Alternatively, narrow bore tubing can be attached to the receptacle by inserting the tubing into the receptacle.

The device may be easily bump tested by injecting a gas to which the gas sensor on the device is sensitive through gas inlet port 502 and into calibration adapter 500 at a concentration above a threshold limit at which the audible and/or visible alarms on the device are set to respond. If exposure to the gas does not activate the alarms, then the device is not appropriate for field use and must be cleaned or reconditioned prior to use.

Calibration adapter 500 also may be used to calibrate the portable safety device. In the calibration process for gas detection devices, a typical initial step is to zero the device with a gas mixture (usually ambient air) free of any components to which the sensor will respond, or which will cause an adverse effect on the sensor. In many cases the zeroing process is performed using clean air and then the user is required to ensure that the device is zeroed in an environment free from significant concentrations of active gases to which the sensor or sensors will respond.

The second part of the calibration process is application of the test gas containing components to which the sensor or sensors is (are) intended to respond. The test gas may be injected through the gas inlet port 502 so that the calibration chamber is filled with the test gas. In some instances, the test gas may be injected as a steady stream so that the concentration in the calibration chamber remains constant. During this stage, the output from the device (display, alarm levels, etc.) is scaled so that the response of the device corresponds to the nominal value of the test gases when exposed to a gas of this concentration. For devices with more than one sensor, or that are designed to detect more than one type of gas, several different gas mixtures may be applied to the device, or alternatively, test gas mixtures containing more than one active component may be used to calibrate the sensors.

Alarm enhancing protective cover 10 and calibration adapter 500 can be used with a wide diversity of gas detection devices that employ a variety of sensor types (e.g. electrochemical, photoionization, catalytic bead, infrared, and optical among others).

FIG. 5 also shows attachment clips 506 that may be used to securely attach the calibration adapter 500 to the cover 10. Attachment clips 506 may engage cover 10 with or without the benefit of mated attachment elements on cover 10. Further, attachment clips 506 may engage cover 10 mechanically using various fasteners such as buckles, clasps, hooks, mated indentations and protrusions, mated protrusions, magnetic snaps, or hook and loop closures.

The presently disclosed invention also relates to a method of amplifying an alarm on a portable safety device which may be a gas monitor. The method comprises attaching an alarm enhancing protective cover, as detailed above, to a portion of a portable safety device having an audible alarm and, optionally, a visible alarm. Once attached, any audible and/or visible signal emitted by the portable safety device may be amplified and redirected toward a user to provide for enhanced signal recognition. That is, the sound chamber of the cover may redirect and amplify sound pressure waves emanating from the audible alarm on the portable safety device causing such sound waves to impinge upon a proximate ear of the user. Further, the visual alarm guide of the cover may redirect any visible signal from the portable safety device causing it to impinge upon a region within the user's field of vision.

The presently disclosed invention further relates to a method to improve efficiency of a device. The method comprises attaching an alarm enhancing protective cover, as detailed above, to a portion of a portable safety device having an audible alarm and optionally a visible alarm, and attaching a calibration adapter, as detailed above, to a portion of the alarm enhancing protective cover such that the calibration adapter forms a calibration chamber which encloses at least one gas sensor. The method further comprises injecting a gas into the calibration chamber through a gas inlet port on the gas calibration adapter, and verifying that the gas will properly activate or trigger an audible or visible alarm on the device. The device may be bump tested if the concentration of the gas that is injected is greater than the threshold concentration expected to activate or trigger the audible and/or visible signals on the device.

Further, the device may be calibrated if the gas is injected at a known concentration which is within the detection range of the device. The user may use the device readings to determine if the device's measurement is sufficiently close to the known concentration of the gas injected and may calibrate the gas sensor on the device accordingly. Calibration may be accomplished by adjusting the output reading, for example, of the device to match that of the known concentration of gas. As noted above, in certain calibration procedures, the device may be zeroed as a first step. This may be achieved using clean air when calibration adapter 500 in not attached to cover 10 on portable safety device 50. Alternatively, the device may be zeroed by attaching calibration adapter 500 to cover 10 on the portable safety device 50 and injecting a gas mixture free of any components to which the sensor will respond. The output from the device (display, alarm levels, etc.) is then scaled so that the response of the device corresponds to a reading of no detected gas or zero.

The previous description is provided to enable persons skilled in the art to practice the various exemplary implementations described herein. Various modifications to these variations will be readily apparent to those skilled in the art, and the generic principles defined herein may be applied to other implementations. All structural and functional equivalents to the elements of the various illustrations and examples in this disclosure that are known or later come to be known to those of ordinary skill in the art are expressly incorporated herein by reference.

EXAMPLES

Several different sound chambers were designed in connection with a cover that engaged an exemplary portable safety device (Tango™ TX1 offered by Industrial Scientific Corporation). Small, medium and large variations where tested using 3D printed parts. Sound pressure was measured from the front and top of the covered device at 3500 Hz for each size variant. Results are shown in Table 1.

TABLE 1

| Sound Pressure (dB) | Without cover | Large | Medium | Small |
|---|---|---|---|---|
| Trial 1: | | | | |
| Front (dB Increase) | 84.6 (0) | 96.6 (12) | 95.6 (11) | 90.5 (5.9) |
| Trial 2: | | | | |
| Front (dB Increase) | 89.6 (0) | 100.7 (11.1) | 98.4 (8.8) | — |
| Top (dB Increase) | 80.8 (0) | 92.8 (12) | 90.2 (9.4) | — |

Based on the above test results and the configuration of the front surface of the specific device used for testing, the sound chamber was narrowed to provide improved access to buttons on the device. The modified sound chamber was again tested using 3D printed parts. Sound pressure from the front of the covered device was measured at 3500 Hz and found to increase by 11.6 dB.

TABLE 2

| | Sound Pressure (dB) From Front | | | Sound Pressure (dB) From Top | | |
|---|---|---|---|---|---|---|
| Unit | Without Cover | With Cover | Increase | Without Cover | With Cover | Increase |
| 1 | 85.1 | 97.2 | 12.1 | 79.6 | 88.1 | 8.5 |
| 2 | 84.6 | 96.2 | 11.6 | 78.4 | 86.4 | 8.0 |
| 3 | 83.3 | 95.2 | 11.9 | 77.7 | 85.3 | 7.6 |
| 4 | 85.9 | 96.2 | 10.3 | 79.0 | 89.4 | 10.4 |
| 5 | 86.1 | 97.4 | 11.3 | 79.4 | 88.0 | 8.6 |
| 6 | 83.9 | 97.4 | 13.5 | 77.0 | 87.1 | 10.1 |
| Average | 84.8 | 96.6 | 11.8 | 78.5 | 87.4 | 8.9 |

A cover which incorporated the additional feature of two visual alarm guides which redirect and amplify the intensity of two visible alarms of the test device was produced. The total increase in sound pressure (dB) observed from the front and top of several different production devices, all with 3 cm$^3$ sound chambers, is shown in Table 2. The cover provides an average increase in sound pressure detected from the front of the portable safety device of 11.8 dB and an average increase from the side of 8.9 dB, all at the resonant frequency of 3500 Hz.

Figure 6:
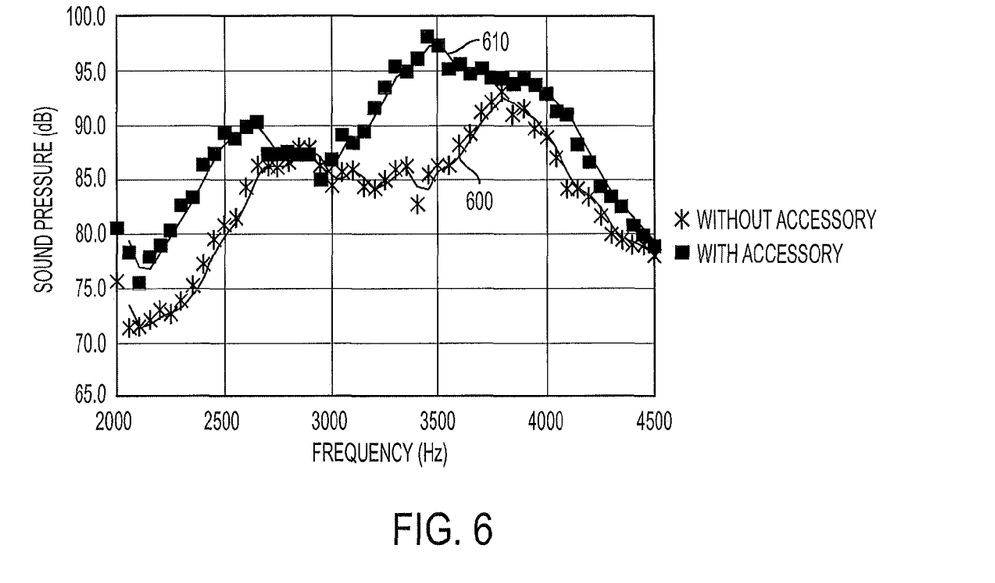
FIG. 6 is a graphical illustration of a frequency response at the front of a portable safety device with and without an alarm enhancing protective cover in accordance with certain aspects of the presently disclosed invention.
Figure 7:
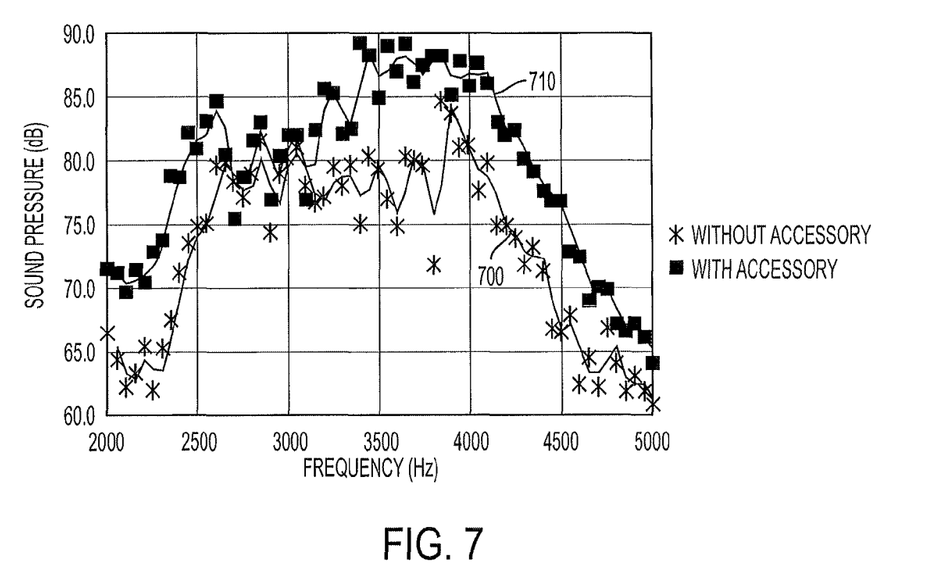
FIG. 7 is a graphical illustration of a frequency response at the top of a portable safety device with and without an alarm enhancing protective cover in accordance with certain aspects of the presently disclosed invention.

The frequency response from a forward facing speaker on the same test device is shown with and without the alarm enhancing protective cover of the present invention in FIGS. 6 and 7. The frequency response detected at the front of the test device (Tango™ TX1 offered by Industrial Scientific Corporation) is shown in FIG. 6: curve 600 provides the frequency response for the test device when uncovered and curve 610 provides the frequency response for the same device with an alarm enhancing protective cover of the presently disclosed invention comprising a 3 cm$^3$ sound chamber. A frequency response improvement in amplitude, in particular, is seen at the resonant frequency of 3500 Hz. The frequency response detected from the top of the same portable safety device is shown in FIG. 7 without (curve 700) and with (curve 710) the same alarm enhancing protective cover used in FIG. 6. A frequency response improvement in amplitude is again seen over the resonant frequency range of 3500 Hz to 4000 Hz.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

We claim:

1. An alarm enhancing protective cover for a portable safety device, said safety device having a case that defines a front face and at least two side faces that are connected to the perimeter of the front face, said front face including a port for the speaker of an audible alarm, said alarm enhancing protective cover comprising:
   a front panel having a sound redirecting surface; and
   side panels that are connected to the perimeter of the front panel, said side panels cooperating with said front panel to define a cavity, the front face and at least a portion of said side faces of the case of said portable safety device being receivable in said cavity, at least one of said side panels having structure for removably engaging respective side faces of the case of the portable safety device such that, at times when said side panels engage the respective sides of the case of the portable safety device, the front panel of said cover, including said sound redirecting surface, is disposed apart from the front face of the cover of the portable safety device to define a sound chamber between the front panel of said cover and the front face of said case, at least one of said side panels at least partially defining an exit opening for said sound chamber with sound being output from the exit opening in response to sound being input to the sound chamber through the port of the front face of said case.

2. The protective cover of claim 1 wherein said front panel partially defines said exit opening such that said at least one side panel and said front panel cooperate to define said exit opening with said exit opening being located adjacent to said sound redirecting surface.

3. The protective cover of claim 1 wherein said sound chamber amplifies sound in the frequency range of 2000 Hertz to 4500 Hertz at the exit opening in response to sound input to the sound chamber through the port of the front face of said casing.

4. The protective cover of claim 3 wherein the redirecting surface of said front panel is located in said sound chamber oppositely from the speaker port of the front face of said case.

5. The protective cover of claim 4 wherein the redirecting surface of said front panel defines a surface that is sloped at an angle with respect to the front face of said case such that said front panel redirects sound entering the sound chamber toward the exit opening of said front panel.

6. The protective cover of claim 5 wherein said redirecting surface redirects sound in a direction that is lateral with respect to the front face of the case of the portable safety device.

7. The protective cover of claim 3 wherein said structure for removably engaging respective side faces of the cover of the portable safety device comprises detent members.

8. The protective cover of claim 3 wherein said structure for removably engaging respective side faces of the cover of the portable safety device comprises fasteners.

9. The protective cover of claim 3 wherein, at times when said side panels of said cover engage the respective sides of the case of the portable safety device, the front panel of said cover is disposed apart from the front face of the cover to define a gap therebetween of at least 0.5 mm.

10. The protective cover of claim 3 wherein, at times when said side panels of said cover engage the respective sides of the case of the portable safety device, the side panels of said cover are disposed apart from respective side faces of the cover to define a gap therebetween of at least 0.5 mm.

11. The alarm enhancing protective cover of claim 3, wherein said sound chamber has an internal volume of about 2.7 cm$^3$ to 3.3 cm$^3$.

12. The alarm enhancing protective cover of claim 3, wherein said sound chamber exit opening defines an opening area of 1.05 cm$^2$ to 1.35 cm$^2$.

13. The alarm enhancing protective cover of claim 3, wherein said redirecting surface of the front panel defines a surface that is oriented at an angle of 40° to 50° with respect to the front face of the case of the safety device.

14. The alarm enhancing protective cover of claim 3, wherein said sound chamber amplifies the sound output from the audible alarm of the portable safety device by about 10 to 12%.

15. The alarm enhancing protective cover of claim 3 wherein said portable safety device further includes an optical alarm, said cover further comprising:
at least one surface that reflects visible light, said light reflecting surface being located on the front panel at a position that is illuminated by the output of said visible alarm on said portable safety device, said light reflecting surface being sloped at an angle with respect to the incidence of light from said optical alarm such that said light reflecting surface of said front panel redirects light from the optical alarm on the portable safety device.

16. The alarm enhancing protective cover of claim 15, wherein said light reflecting surface of the front panel defines an angle of 40° to 50° with respect to the front face of the case of said portable safety device.

17. The alarm enhancing protective cover of claim 15, wherein said light reflecting surface of the front panel is a mirrored surface.

18. The alarm enhancing protective cover of claim 3, wherein said protective cover is comprised of high-impact molded material.

19. The alarm enhancing protective cover of claim 3, wherein said cover has at least one opening that permits access to at least one of a button, a viewing screen, a sensor, a light and an access point that are located on the portable safety device at times when said side panels of the cover engage the respective sides of the case of the portable safety device.

20. The alarm enhancing protective cover of claim 19, wherein said sensor located on the portable safety device is a gas sensor.

21. The alarm enhancing protective cover of claim 3, wherein said portable safety device is a portable gas monitor.

22. The alarm enhancing protective cover of claim 3, further comprising:
a calibration adapter that has side walls and a gas inlet port, the side walls of said calibration adapter being adapted to removeably engage a front portion of said protective cover, said calibration adapter covering the exit opening in said cover at times when the side walls of said calibration adaptor engage said protective cover, said calibration adapter cooperating with said case of said portable safety device at times when said side panels engage the respective sides of the case of portable safety device and with said protective cover at times when said side walls engage the protective cover to define a calibration chamber.

23. The alarm enhancing protective cover of claim 22, wherein said calibration chamber is in communication with a gas sensor in the portable safety device.

24. A method of amplifying an alarm on a portable safety device, said method comprising the steps of:
attaching an alarm enhancing protective cover to a portable safety device that includes an audible alarm having a speaker port that is located on a front face of the portable safety device, wherein said protective cover includes a front panel that has a sound redirecting surface and side panels that are connected to the perimeter of the front panel, said side panels cooperating with said front panel to define a cavity, the front face and at least a portion of said side faces of the case of said portable safety device being receivable in said cavity, the side panels having structure for removably engaging respective side faces of the case of the portable safety device such that, at times when said side panels engage the respective sides of the case of the portable safety device, the front panel of said cover, including said sound redirecting surface, is disposed apart from the front face of the case of the portable safety device to define a sound chamber between the front panel of said cover and the front face of said case at least one of said side panels at least partially defining an exit opening to said sound chamber; and providing sound to said sound chamber through the port in the front face of said case to generate an amplified sound at the exit opening.

25. The method of claim 24 wherein said sound chamber provides amplified sound in the frequency range of between 2000 Hertz and 4500 Hertz.

26. The method of claim 24 further comprising the step of redirecting the sound provided to said sound chamber from the port in the front face of said case from a location that is opposite from the speaker port.

27. The method of claim 26 wherein the sound is redirected at an angle with respect to the front face of the portable safety device such that said front panel redirects sound from the speaker on the portable safety device in a lateral direction with respect to the front face of the case of the portable safety device.

28. The method of amplifying an alarm on a portable safety device of claim 24, wherein said sound chamber amplifies the sound output from the audible alarm on the portable safety device by about 10 to 12%.

29. A method to improve the effectiveness of a portable safety device, said method comprising the steps of:
attaching an alarm enhancing protective cover to a portable safety device that includes an audible alarm having a speaker port that is located on a front face of the portable safety device, wherein said protective cover includes a front panel that has a sound redirecting surface and side panels that are connected to the perimeter of the front panel, said side panels cooperating with said front panel to define a cavity, the front face and at least a portion of said side faces of the case of said portable safety device being receivable in said cavity, the side panels having structure for removably engaging respective side faces of the case of the portable safety device such that, at times when said side panels engage the respective sides of the case of the portable safety device, the front panel of said cover, including said sound redirecting surface, is disposed apart from the front face of the case of the portable safety device to define a sound chamber between the front panel of said cover and the front face of said case at least one of said side panels at least partially defining an exit opening to said sound chamber;
attaching a calibration adapter to a front portion of the alarm enhancing protective cover, said calibration adapter having a gas inlet port and side walls that are adapted to removeably engage a front portion of said protective cover to cover the exit opening said protective cover at times when the side walls of said calibration adaptor engage said protective cover, said calibration adapter cooperating with said cover of said portable safety device at times when said side panels engage the respective sides of the portable safety device and with said protective cover at times when said side walls engage the protective cover to define a calibration chamber that is in communication with said gas inlet port;
injecting gas having at least one constituent of known concentration into the calibration chamber through said gas inlet port; and
determining the accuracy of the portable safety device with respect to the at least one constituent gas of known concentration.

30. The method to improve the effectiveness of a portable safety device of claim 29, further comprising:
verifying that the audible alarm on the portable safety device is activated when said at least one constituent gas of known concentration is greater than a threshold concentration required to trigger the audible alarm of the portable safety device.

31. The method to improve the effectiveness of a portable safety device of claim 29, further comprising:
determining if an output reading from the portable safety device is consistent with the known concentration of the gas; and
calibrating at least one gas sensor within the portable safety device so that the measurement of the gas concentration by the portable safety device corresponds to the known concentration of the gas.

32. The method of calibrating a portable safety device of claim 31, wherein said calibrating step comprises adjusting the output of the at least one gas sensor to correspond to the known concentration of the gas.

* * * * *